(12) United States Patent
Martin

(10) Patent No.: US 6,479,502 B1
(45) Date of Patent: Nov. 12, 2002

(54) HYDROXAMIC ACID DERIVATIVES AS PROTEINASE INHIBITORS

(75) Inventor: Fionna Mitchell Martin, Oxford (GB)

(73) Assignee: British Biotech Pharmaceuticals, Oxford (GB)

( * ) Notice: Subject to any disclaimer, the term of this patent is extended or adjusted under 35 U.S.C. 154(b) by 0 days.

(21) Appl. No.: 09/763,424

(22) PCT Filed: Aug. 27, 1999

(86) PCT No.: PCT/GB99/02826
§ 371 (c)(1),
(2), (4) Date: Feb. 21, 2001

(87) PCT Pub. No.: WO00/12477
PCT Pub. Date: Mar. 9, 2000

(30) Foreign Application Priority Data

Aug. 29, 1998 (GB) ............................................. 9818830
Dec. 23, 1998 (GB) ............................................. 9828525

(51) Int. Cl.$^7$ ................. A61K 31/4375; A61K 31/438; A61K 31/4523; C07D 211/96; C07D 471/04

(52) U.S. Cl. ................. 514/292; 546/244; 546/247; 546/248; 546/193; 546/223; 546/233; 546/153; 546/122; 546/81; 546/82

(58) Field of Search ................................ 546/244, 247, 546/248, 193, 223, 233, 153, 122, 82, 81, 102, 104, 105; 514/318, 317, 329, 331, 292, 293, 297, 300, 312

(56) References Cited

FOREIGN PATENT DOCUMENTS

| WO | WO 98/05635 | 2/1998 |
| WO | WO 99/24399 | 5/1999 |

OTHER PUBLICATIONS

Decicco, C.P., et al.: "Amide Surrogates of Matrix Metalloproteinase Inhibitors: Urea and Sulfonamide Mimics", Bioorganic & Medicinal Chemistry Letters, vol. 7, No. 18, Jan. 1, 1997, pp. 2231–2236, XP002071089.

*Primary Examiner*—Mark L. Berch
*Assistant Examiner*—Kahsay Habte
(74) *Attorney, Agent, or Firm*—Banner & Witcoff LLP

(57) ABSTRACT

Compounds of formula (I) are matrix metalloprotemase inhibitors wherein X represents a carboxylic acid group —COOH, or a hydroxamic acid group —CONHOH; $R_2$ represents a radical of formula (II): $R_3$—$(ALK)_m$—$(Q)_p$—$(ALK)_n$-, and W represents a cyclic amino radical of formula (IIIA) or (IIIB):

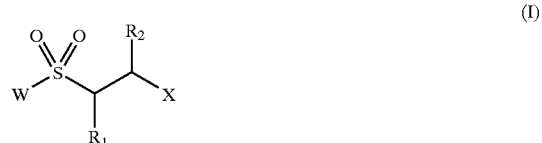

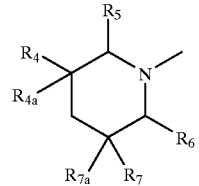

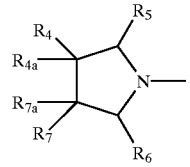

9 Claims, No Drawings

HYDROXAMIC ACID DERIVATIVES AS PROTEINASE INHIBITORS

This invention relates to novel hydroxamic acid and carboxylic acid derivatives which are inhibitors of matrix metalloproteinases to pharmaceutical compositions comprising such compounds and to their use in the treatment of diseases and conditions responsive to modulation of matrix metalloproteinase activity.

BACKGROUND TO THE INVENTION

The matrix metalloproteinases (MMPs) are a family of enzymes including interstitial collagenase, neutrophil collagenase, collagenase-3, 72kDa gelatinase, 92kDa gelatinase, stromelysin-1, stromelysin-2, stromelysin-3, matrilysin, macrophage metalloelastase, membrane-type metalloproteinase-1 and membrane-type metalloproteinase-2. These enzymes share a common zinc-containing catalytic domain and a pro-sequence which maintains latency. A wide range of cells and tissues can express MMPs in response to activation by inflammatory stimuli such as interleukin-1 or tumour necrosis factor-α (TNF-α). Different stimuli can induce overlapping yet distinct repertoires of MMPs and different cell types can respond to the same stimuli by expression of distinct combinations of MMPs. MMPs can degrade the protein components of extracellular matrix such as collagens, vitronectin and elastin, and have recently been shown to process membrane proteins such as pro-TNF-α to release soluble TNF-α. MMPs are thought to play a central role in the pathology of inflammatory diseases such as rheumatoid arthritis as well as in the growth and metastasis of tumours.

Compounds which have the property of inhibiting the action of MMPs are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal venous, diabetic or gastric ulceration, ulcerative colitis, Crohn's disease, pressure sores, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases which include arthritic conditions and solid tumour growth as well as psoriasis, proliferative retinopathies, neovascular glaucoma, ocular tumours, angiofibromas and hemangiomas, cardiac and cerebral infarction, and wound healing.

A known class of collagenase inhibitors is represented by those disclosed in EP-A-0574758 (Roche), EP-A-0684240 (Roche), and WO 95/33731 (Roche). In general, the compounds disclosed in those publications may be represented by the structural formula (IA):

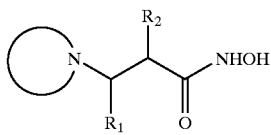

(IA)

in which $R_1$, $R_2$ and the N-containing ring are variable in accordance with the specific disclosures of the publications.

Another known class of MMP inhibitors is represented by those disclosed in EP-A-0606046 (Ciba-Geigy) WO 96/00214 (Ciba-Geigy), WO 95/35275 (British Biotech) and WO 95/35276 (British Biotech), which in general may be represented by the structural formula (IB):

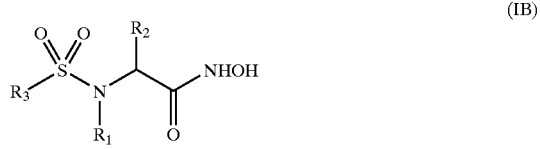

(IB)

in which $R_1$, $R_2$ and and $R_3$ are variable in accordance with the specific disclosures of the publications.

WO 99/24399 (Darwin Discovery Ltd), published May 20, 1999, discloses MMP inhibitors inter alia of structural formula (IC)

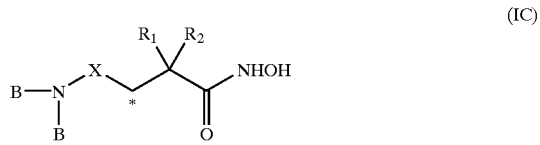

(IC)

wherein X is —SO$_2$— or —SO—, and $R_1$, $R_2$ and each B is as defined in the document.

BRIEF DESCRIPTION OF THE INVENTION

The present invention makes available a new class of inhibitors of MMPs which, as a result of that activity, are useful in the management of diseases or disorders associated with over production of or over responsiveness to MMPs. The compounds of the invention differ in structure from those of WO 99/24399 inter alia in that the methylene group equivalent to that marked with an asterisk in formula (IC) is substituted in the present compounds.

DETAILED DESCRIPTION OF THE INVENTION

According to the present invention there is provided a compound of formula (I)

(I)

wherein
  X represents a carboxylic acid group —COOH, or a hydroxamic acid group —CONHOH;
  $R_2$ represents a radical of formula (II)

$$R_3-(ALK)_m-(Q)_p-(ALK)_n-$$ (II)

wherein
  $R_3$ represents hydrogen or an optionally substituted cycloalkyl, optionally substituted cycloalkenyl, optionally substituted aryl, or optionally substituted heterocyclic ring having 5 or 6 ring members,
  each ALK independently represents an optionally substituted divalent $C_1$–$C_3$ alkylene radical,
  Q represents —O—, —S—, —S(O)—, —S(O$_2$)—, —C(O)O—, —OC(O)— or —N(R$_9$)—wherein R$_9$ is hydrogen, $C_1$–$C_6$alkyl, or $C_1$–$C_6$alkoxy, and
  m, n and p are independently 0 or 1;

$R_1$ represents a radical of formula (II) as defined for $R_2$, except that $R_1$ is not hydrogen;

W represents a cyclic amino radical of formula (IIIA) or (IIIB):

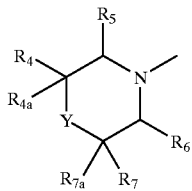

(IIIA)

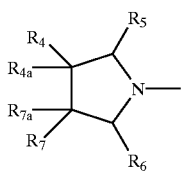

(IIIB)

wherein

Y represents —O—, —S—, —S(O)—, —S($O_2$)—, —N($R_8$)—, or —(CH($R_8$))—, or —(C=N-$R_8$)— wherein $R_8$ is a radical of formula (II) as defined in relation to $R_2$; and (i) $R_4$, $R_5$ $R_6$ and $R_7$ each independently represents a radical of formula (II) as defined in relation to $R_2$, and $R_{4a}$ and $R_{7a}$ each independently represent hydrogen or $C_1$–$C_3$ alkyl, or (ii) $R_4$, $R_{4a}$ and $R_5$ taken together with the carbon atoms to which they are attached form an optionally substituted benzene or pyridine ring fused to the cyclic amine ring, $R_{7a}$ represents hydrogen or $C_1$–$C_3$ alkyl, and $R_6$ and $R_7$ each independently represents a radical of formula (II) as defined in relation to $R_2$, or (iii) $R_4$, $R_{4a}$ and $R_5$ taken together with the carbon atoms to which they are attached form an optionally substituted benzene or pyridine ring fused to the cyclic amine ring, $R_6$, $R_7$ and $R_{7a}$ taken together with the carbon atoms to which they are attached also form an optionally substituted benzene or pyridine ring fused to the cyclic amine ring, or (iv) when W is a cyclic amino radical of formula (IIIA) wherein Y is —(CH($R_8$))—, then $R_4$ $R_{4a}$ and $R_8$ taken together with the carbon atoms to which they are attached form an optionally substituted benzene or pyridine ring fused to the cyclic amine ring, $R_{7a}$ represents hydrogen or $C_1$–$C_3$ alkyl, and $R_5$, $R_6$ and $R_7$ each independently represents a radical of formula (II) as defined in relation to $R_1$ and $R_2$, or (v) when W is a cyclic amino radical of formula (IIIB) then $R_4$, $R_{4a}$, $R_7$ and $R_{7a}$ taken together with the carbon atoms to which they are attached form an optionally substituted benzene or pyridine ring fused to the cyclic amine ring, and $R_5$ and $R_6$ each independently represents a radical of formula (II) as defined in relation to $R_1$ and $R_2$, or a pharmaceutically acceptable salt, hydrate or solvate thereof.

As used herein the term "$C_1$–$C_3$alkyl" means a straight or branched chain alkyl moiety having from 1 to 3 carbon atoms, including for example, methyl, ethyl and n-propyl.

As used herein the term "divalent $C_1$–$C_3$alkylene radical" means a saturated hydrocarbon chain having from 1 to 3 carbon atoms and two unsatisfied valencies.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "cycloalkenyl" means a saturated alicyclic moiety having from 5–8 carbon atoms and at least one double bond, and includes, for example, cyclopentenyl, cyclohexenyl, cycloheptenyl and cyclooctenyl.

As used herein the term "aryl" means a mono-, bi- or tri-cyclic carbocyclic aromatic group, and includes groups consisting of two covalently linked monocyclic carbocyclic aromatic groups. Illustrative of such groups are phenyl, biphenyl and napthyl.

As used herein, the term $C_3$–$C_8$ carbocyclic ring means a ring of 3 to 8 carbon atoms, with no heteroatom as part of the ring. The term includes aromatic (aryl) and non aromatic (non aryl) carbocyclic rings, for example the benzene ring and cycloalkyl rings.

As used herein the term "heteroaryl" refers to a 5- or 6-membered aromatic ring containing one or more heteroatoms, and optionally fused to a benzyl or pyridyl ring; and to groups consisting of two covalently linked 5- or 6- membered aromatic rings each containing one or more heteroatoms; and to groups consisting of a monocyclic carbocyclic aromatic group covalently linked to a 5- or 6-membered aromatic rings containing one or more heteroatoms, Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

As used herein the terms "heterocyclic ring having 5 or 6 ring members" "heterocyclyl" or "heterocyclic" includes "heteroaryl" as defined above, and in addition means a 5 or 6 membered aromatic or non-aromatic heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido and 1,3-dioxo-1,3-dihydro-isoindol-2-yl groups.

Where any group herein is referred to as "optionally substituted" this means the group may be unsubstituted or substituted with at least one substituent selected from ($C_1$–$C_3$)alkyl, ($C_1$–$C_3$)alkoxy, oxo, phenyl, phenoxy, hydroxy, mercapto, ($C_1$–$C_6$)alkylthio, amino, halo (including fluoro, chloro, bromo and iodo), trifluoromethyl, cyano, nitro, —COOH, —CONH$_2$, —COO$R^A$, —NHCO$R^A$, —CONH$R^A$, NH$R^A$, N$R^A R^B$, or —CON$R^A R^B$ wherein $R^A$ and $R^B$ are independently ($C_1$–$C_3$)alkyl.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are at least two actual or potential chiral centers in the compounds according to the invention because of the presence of asymmetric carbon atoms. The presence of several asymmetric carbon atoms gives rise to a number of diastereomers with R or S stereochemistry at each chiral center. The invention includes all such diastereomers and mixtures thereof.

In the compounds of the invention:

X is a carboxylic acid group —COOH, or a hydroxamic acid group —CONHOH;

$R_1$ may be, for example, an optionally substituted $C_1$–$C_6$alkyl, phenyl, or phenyl($C_1$–$C_6$alkyl)— group;

$R_2$ may be, for example hydrogen, or an optionally substituted $C_1$–$C_6$alkyl, phenyl($C_1$–$C_6$alkyl)— group, or an optionally substituted heterocyclic group;

W may be, for example a radical of formula (IIIC), (IIID) or (IIIE)

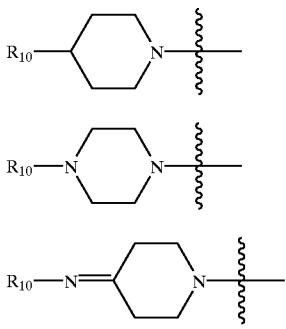

(IIIC)

(IIID)

(IIIE)

wherein $R_{10}$ is as defined in relation to $R_2$ in formula (I), for example an optionally substituted phenyl, biphenyl, phenyl($C_1$–$C_6$alkyl)—, phenoxy, phenoxy ($C_1$–$C_3$)alkyl, or heterocyclic group;

Thus, examples of compounds of the invention include those wherein

X is a carboxylic acid group —COOH, or a hydroxamic acid group —CONHOH;

$R_1$ is n-propyl, iso-propyl n-butyl, iso-butyl, benzyl, phenylethyl, 4-fluorobenzyl, or 4-fluorophenylethyl;

$R_2$ is hydrogen, n-propyl, n-butyl, iso-butyl, benzyl, phenylethyl, tetrahyd ropyranyl, 1-(3,4,4-trimethyl-2,5-dioxoimidazolidin-1-yl)propyl, or 1-(phthalimido)-propyl;

W is a radical of formula (IIIC), (IIID), or (IIIE) wherein $R_{10}$ is n-propyl, n-butyl or iso-butyl; or a phenyl, phenoxy, benzyl, phenylethyl, phenylpropyl, . phenoxy, or phenoxymethyl group, any of which may be substituted in the phenyl ring, for example in the 4-position, by chloro, fluoro, methoxy or cyano; pyridinyl or pyridinyloxy either of which may be substituted by chloro, fluoro, methoxy or cyano; or biphenyl or 4-pyridinylphenyl, either of which may be substituted in either ring by chloro, fluoro, methoxy or cyano. Examples of W radicals include 4-phenylmethylpiperidinyl, 4 methylpiperidinyl, 4-(4-methylphenyl)piperidinyl, 4-(4-chlorophenoxy) piperidinyl, 4-phenylpiperidinyl, 4(4-fluorophenyl) piperidinyl, 4-(4-fluorophenoxy)piperidinyl, 4-(4-pyridinyloxy)-piperidinyl, 4-(4-cyanophenyloxy) piperidinyl, 4-(4-cyanophenoxyimino)-piperdinyl, 4-(4'-chloro-biphenyl4-yl)-piperdinyl, 4-(2-chloro-biphenyl-4-yl) piperdinyl, 4-(4-fluorophenylmethyl) piperidinyl, 4-(4-fluorophenoxymethyl)-piperidinyl, 4-phenylpiperazinyl, 4-(4-fluorophenyl)piperazinyl, 4-(4-pyridinyl-methyl)piperazinyl, 4-(4-chlororophenyl)piperazinyl, 4-pyridin-4-ylpiperazinyl, 4-phenylmethylpiperazinyl, and 4-(4-fluorophenylmethyl)piperazinyl.

Specific examples of compounds in accordance with the invention include those named and characterised in the Examples herein, and pharmaceutically acceptable salts, hydrates or solvates thereof. One interesting compound of the invention is 3-[4-(4-fluoro-phenoxymethyl)-piperidine-1-sulfonyl]-N-hydroxy-4-phenyl-butyramide, and its pharmaceutically acceptable salts, hydrates and solvates. This compound is an inhibitor of collagenase-3 (MMP-13), in particular. Another interesting compound of the invention is 3-(4-benzyl-piperidine-1-sulfonyl)-N-hydroxy4-phenyl-butyramide, and its pharmaceutically acceptable salts, hydrates and solvates. This compound is an inhibitor of gelatinase A, in particular.

Compounds of the invention wherein X is a hydroxamic acid group may be prepared by a process which comprises causing a carboxylic acid of the invention of general formula (IV)

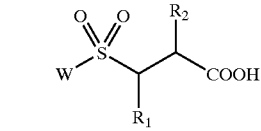

(IV)

or an activated derivative thereof to react with hydroxylamine, O-protected hydroxylamine, N,O-diprotected hydroxylamine, or a salt thereof, W, $R_1$ and $R_2$ being as defined in general formula (I), and subsequently removing any protecting groups from the hydroxylamine moiety Conversion of (IV) to an activated derivative such as the pentafluorophenyl, hydroxysuccinyl, or hydroxybenzotriazolyl ester may be effected by reaction with the appropriate hydroxy compound in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Examples of O-protected hydroxylamines for use in the process of the invention above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in the process of the invention include N,O-bis(benzyl) hydroxylamine, N,O-bis(4-methoxybenzyl)hydroxylamine, N-tert-butoxycarbonyl-O-tert-butyidimethylsilylhydroxylamine, N-tert-butoxycarbonyl-O-tetrahydropyranylhydroxylamine, and N,O-bis(tert-butoxycarbonyl)hydroxylamine.

Carboxylic acids of formula (IV) may be prepared by condensation of a sulfinyl chloride of formula (V) or a sulfonyl chloride of formula (VA)

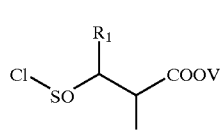

(V)

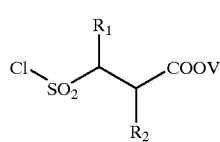

(VI)

wherein V is a carboxyl protecting group and $R_1$ and $R_2$ are as defined with respect to formula (I), with a cyclic amine W-H wherein W is as defined with respect to formula (I) followed, in the case of the sulfinyl chloride (V), by oxidation of the sulfinyl group to a sulfonyl group and, in each case, thereafter removing the protecting group V.

Sulfinyl chlorides of formula (V) may be prepared by reaction of an acetylthio compound of formula (VI)

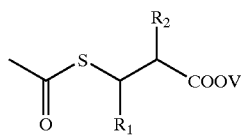
(VI)

wherein V is a carboxyl protecting group and $R_1$ and $R_2$ are as defined with respect to formula (I), with sulfuryl chloride in the presence of acetic anhydride.

Sulfonyl chlorides of formula (VA) may be prepared by reaction of an acetylthio compound of formula (VI) as defined above, with chlorine and aqueous acetic acid.

Acetylthio compounds of formula (VI) may be prepared by reaction of an αβ-unsaturated carboxylic acid of formula (VII)

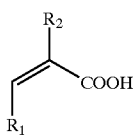
(VII)

wherein $R_1$ and $R_2$ are as defined with respect to formula (I), with thiolacetic acid, followed by protection of the carboxylic acid group.

The preparative Examples herein give further details of the reaction conditions for the preparation of compounds of the invention and intermediates there of.

As mentioned above, the compounds of the invention are inhibitors of matrix metalloproteinases and therefore of value in the treatment of disease states or conditions resulting from over production of, or over responsiveness to, MMPs.

Accordingly in another aspect, this invention concerns:
(i) a method of treatment of conditions in mammals, in particular in humans, resulting from over production of or over responsiveness to MMPs, which method comprises administering to the mammal an effective amount of a compound as defined with respect to formula (I) above; and
(ii) a compound as defined with respect to formula (I) for use in human or veterinary medicine treatment of conditions resulting from over production of or over responsiveness to MMPs; and
(iii) the use of a compound as defined with respect to formula (I) in the preparation of an agent for treatment of conditions in mammals, in particular in humans, resulting from over production of or over responsiveness to MMPs.

Conditions resulting from over production of or over responsiveness to MMPs include rheumatoid arthritis, osteoarthritis, osteopenias such as osteoporosis, periodontitis, gingivitis, corneal. Epidermal, venous, diabetic or gastric ulceration, ulcerative colitis, Crohn's disease, pressure sores, tumour metastasis, invasion and growth, multiple sclerosis, angiogenesis dependent diseases, which include arthritic conditions and solid tumour growth as well as psoriasis, proliferative retinopathies, neovascular glaucoma, ocular tumours, angiofibromas and hemangiomas.

According to a further aspect of the invention there is provided a pharmaceutical or veterinary formulation comprising a compound of general formula (I) and a pharmaceutically and/or veterinarily acceptable carrier. One or more compounds of general formula (I) may be present in association with one or more non-toxic pharmaceutically and/or veterinarily acceptable carriers and/or diluents and/or adjuvants and if desired other active ingredients.

Compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

For treatment of the respiratory tract, the active ingredient (s) may be made up as inhaleable aerosols or sprays in which the compound is dissolved or suspended, or as inhaleable powders, by conventional formulation methods.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples illustrate embodiments of the invention. The starting α,β-unsaturated acids are either commercially available or may be prepared by known literature methods. In the Examples, the following abbreviations have been used:
DCM Dichloromethane
DMAP 4-Dimethylaminopyridine
DMF N,N-Dimethylformamide
EDC N-Ethyl-N[1]-(3-dimethylaminopropyl) carbodiimide hydrochloride
EtOAc Ethylacetate
EtOH Ethanol
HOBt 1-Hydroxybenzotriazole
MeOH Methanol
NalO$_4$ Sodium periodate
NaOH Sodium hydroxide
NMM N-Methyl morpholine
Ph$_3$PO Triphenyl phospine oxide
RuCl$_3$.xH$_2$O Ruthenium (Ill) chloride hydrate
TEA Triethylamine
TFA Trifluoroacetic acid
TLC Thin layer chromatography $^1$H and $^{13}$C NMR spectra were recorded using either a Bruker DPX250 spectrometer at 250.1 and 62.9 MHz respectively, or a Bruker AMX2 500 spectrometer at 500.1 and 125.7 MHz respectively. Mass spectra were obtained on a PE-SCIEX API 165 with a turbo ion spray interface. Infra red spectra were obtained on a Perkin Elmer 1600 series FTIR machine. All organic solutions were dried over MgSO$_4$.

EXAMPLE 1

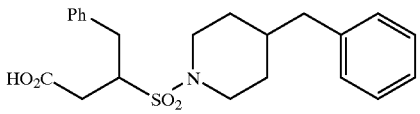

3-(4-Benzy-piperidine-1-sulfonyl )-4-phenyl-butyric Acid.

STEP A
5-Phenyl-but-2-enoic Acid

Tert-butoxycarbonylmethylene triphenyl phosphonium bromide (22.16 g, 48.5 mmol) was suspended in water (100 mL) and DCM (50 mL) and basified with 2M NaOH (against phenolphthalein indicator). The layers were separated and the aqueous layer re-extracted with DCM. The DCM extracts were combined, dried, filtered and evaporated under reduced pressure to give a gummy solid. This was re-suspended in benzene (50 mL) with stirring and cooled to 0° C. Phenylacetaldehyde (5.76 g, 48 mmol) was added and the reaction warmed to room temperature and stirred overnight. The precipitated Ph$_3$PO was filtered off and the filtrate concentrated in vacuo. The resulting residue was stirred in hexanes and re-filtered. The filtrate was again concentrated under reduced pressure to give 3-(4-Benzy-piperidine-1-sulfonyl)-4-phenyl-butyric acid tert-butyl ester as a yellow oil (8.29 g, 38 mmol). This was taken up in DCM with stirring and cooled to 0° C. TFA (10 mL) was added and the reaction placed in the fridge overnight. The solvents were evaporated under reduced pressure to give the title compound as a semi-solid (6.66 g, Quant.) $^1$H-NMR δ (CDCl$_3$) 7.48–7.16 (6H, m), 5.79 (1H, d, J=15.6 Hz), 3.55 (2H, d, J=6.7 Hz).

STEP B
3-Acetylsulfanyl-4-phenyl-butyric Acid.

Thiolacetic acid (9.3 mL, 131 mmol) was added to 4-phenyl-but-2-enoic acid (4.25 g, 26.2 mmol) under an argon atmoshere. The resulting solution stirred with the exclusion of light at room temperature for 48 h. The solvent was evaporated to yield an orange oil (6.26 g, Quant). $^1$H-NMR δ (CDCl$_3$), 7.25 (5H, m), 4.09 (1H, m), 2.99 (2H, d, J=6.4 Hz), 2.66(2H, d, J=6.4 Hz) and 2.30 (3H, s).

STEP C
3-Acetylsulfanyl-4-phenyl-butyric Acid Benzyl Ester.

The product from Step B (5.4 g, 26.2 mmol) was taken up in DCM (50 mL) with stirring and cooled to 0° C. EDC (6.0 g, 31.4 mmol) and DMAP (164 mg, 1.31 mmol) were added followed by benzyl alcohol (2.4 mL, 23.6 mmol). The resulting solution was stirred at room temperature overnight with the exclusion of moisture. The reaction was diluted with DCM and washed successively with 1 M HCl, water, 5% Na$_2$CO$_3$ solution, brine and dried, filtered and evaporated to give a dark oil. This was purified by silica gel column chromatography eluting with hexane/ethyl acetate 1:1 to give the product as an orange oil (5.98 g, 70%). $^1$H-NMR δ (CDCl$_3$) 7.38–7.17 (10H, m); 5.11 (2H, s), 4.08 (1H, m), 2.96 (2H, d, J=6.4 Hz), 2.64 (2H, d, J=6.4 Hz) and 2.27 (3H, s).

STEP D
3-(4-Benzyl-piperidine-1-sulfinyl)-4-phenyl-butyric Acid Benzyl Ester.

The product from Step C (670 mg, 2.05 mmol) was taken up in dry DCM (5 mL) with stirring and cooled to −15° C. under argon atmosphere. Acetic anhydride (193 μL, 2.05 mmol) and sulfuryl chloride (329 μL, 4.1 mmol) were added via a syringe. After being stirred for 1 h, the mixture was concentrated in vacuo at room temperature. The sulfinyl chloride thus obtained was used for coupling without purification. A solution of 4-benzyl piperidine (370 μL, 2.11 mmol) in dry DCM (5 mL) and NMM (232 μL, 2.11 mmol) was added via a cannular to a stirred solution of the sulfinyl chloride in dry DCM (10 mL) at 0° C. under an argon atmosphere. The mixture was allowed to warm to room temperature and stirred overnight. The solvent was evaporated to give an oil which was purified by silica gel column chromatography eluting with hexane/ethyl acetate 1:1. This gave the product as a mixture of diastereoisomers (430 mg, 44%). $^1$H-NMR δ (CDCl$_3$) 7.38–7.08 (15H, m), 5.05 (2H, m), 3.55 (1H, m), 3.41–3.25 (2H, m), 3.01–2.42 (7H, m), 1.67 (1H, m) and 1.26 (2H, m).

STEP E
3-(4-Benzyl-piperidine-1-sulfonyl)-4-phenyl-butyric Acid Benzyl Ester.

The product from Step D (430 mg, 0.91 mmol) was taken up in acetonitrile (1.5 mL) with stirring and cooled to 0° C. RuCl$_3$.3H$_2$O (0.5 mg) and NalO$_4$ (290 mg, 1.37 mmol) were added followed by water (2 mL). The resulting mixture was stirred at room temperature for 2½h until tlc (hex/EtOAc 1:1) indicated the absence of starting material. The reaction was diluted with DCM, the layers separated and the aqueous layer was further extracted with DCM. The organic extracts were combined, dried, filtered and concentrated in vacuo to give the product as an oil (360 mg, 81%). $^1$H-NMR δ (CDCl$_3$) 7.37–7.09 (15H, m), 4.96 (1H, d, J=12.2 Hz), 4.94 (1H, d, J=12.1 Hz), 3.91 (1H, m), 3.89–3.68 (2H, m), 3.31 (1H, dd, J=4.5, 14.0 Hz), 2.88–2.45 (7H, m 1.72–1.50 (3H, m) and 1.29–1.15 (2H, m).

STEP F 3-(4-Benzyl-piperidine-1-sulfonyl)4-phenyl-butyric Acid.

The product from Step E (360 mg, 0.73 mmol) was taken up in EtOAc (10 mL) with stirring under a blanket of argon. 10% palladium on charcoal (130 mg) was added. The resulting suspension was hydrogenated in a PARR apparatus at room temperature overnight. The system was purged with argon and the catalyst removed by filtration. The filtrate was evaporated under reduced pressure to give the desired product as a gum (292mg, Quant). $^1$H-NMR δ(MeOD) 7.24–7.10 (10H, m), 3.89 (1H, m), 3.69 (2H, m), 3.25 (1H, dd, J=4.8, 17.1 Hz), 2.81–2.64 (4H, m), 2.53 (2H, d, J=6.7 Hz), 2.45 (1H, dd, J=4.8, 17.1 Hz), 1.61 (3H, m) and 1.28 (2H, m). $^{13}$C-NMR δ(MeOD) 174.3, 141.7, 138.8, 130.8, 130.6, 130.2, 129.7, 128.4, 127.4, 61.0, 47.6, 44.2, 39.2, 36.6, 34.8, 33.7. ESMS=(M+1) 402.2, (M−1) 400.0.

EXAMPLE 2

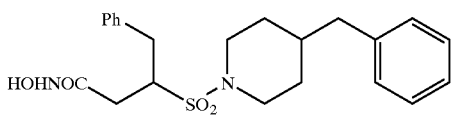

3-(4-Benzyl-piperidine-1-sulfonyl)-N-Hydroxy-4-phenyl-butyramide.

STEP G 3-(4-Benzyl-piperidine-1-sulfonyl)-N-Hydroxy-4-phenyl-butyramide.

The product from Step F (292 mg, 0.73 mmol) was taken up in DMF (5 mL) with stirring and cooled to 0° C. and HOBt (124 mg, 0.92 mmol) followed by EDC (176 mg, 0.92 mmol) were added. After 1h at 0° C. hydroxylamine hydrochloride (161 mg, 2.31 mmol) and NMM (254 μL, 2.31 mmol) were added. The reaction was allowed to warm to room temperature and stirred overnight. The solvent was removed in vacuo and the residue was purified by reverse phase HPLC to give the desired product as a white solid (21 mg). $^1$H-NMR δ(MeOD) 7.33–7.11 (10H, m), 4.00 (1H, m), 3.68 (2H, m), 3.23 (1H, dd, J=4.9, 14.1 Hz), 2.76 (3H, m), 2.51 (3H, m), 2.21 (1H, dd, J−4.9, 14.1 Hz), 1.63 (3H, m) and 1.20 (2H, m). $^{13}$C-NMR δ(MeOD) 169.5, 141.7, 138.9, 130.8, 130.6, 130.2, 129.7, 128.4, 127.4, 60.0, 47.4, 44.2, 39.2, 36.7, 33.6, 33.3. IR V$_{max}$ (reflection disc) 2921, 1665, 1447, 1309, 1137, 940, 747. ESMS=(M+1) 417.0, (M+TFA−1) 529.2, (M−1) 415.0.

The compounds of Examples 3 to 18 were prepared by modification of the methods described for Examples 1 and 2 as indicated in the text. The starting α,β-unsaturated acids if not commercially available maybe prepared from commercially available aldehydes and ylides as described in Step A. The substituted piperidine derivatives or other amines required are either commercially available or may be prepared by known literature methods (Perregaard, J; Moltzen, E. K; Meier, E; Sanchez, C; *J. Med. Chem.* 1995, 38, 1998–2008 and by using the Mitsonobu reaction conditions in Gowravaram, M. R; Tomczuk, B. E; Johnson, J. S; Delecki, D; Cooke, E. R; Ghose, A. K; Mathiowetz, A. M; Spurlino, J. C; Rubin, B; Smith, D. L; Pulvino, T; Wahl, R. C; *J. Med. Chem.* 1995, 38, 2570–2581).

EXAMPLE 3

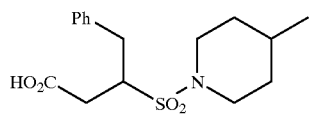

3-(4-Methyl-piperidine-i-sulfonyl)-4-phenyl-butyric Acid

STEP H

3-Chlorosulfonyl4-phenyl-butyric Acid Benzyl Ester

The product from Step C (1.20 g, 3.66 mmol) was suspended in a 5% acetic acid water solution (50 mL) with stirring and cooled to 0° C. Chlorine gas was bubbled through this cooled suspension for 15 min. Reaction was stirred at 0° C. was a further 20 min and then the excess chlorine was removed by bubbling argon through the suspension. the product was extracted into DCM. The DCM extract was was washed with water (X3), brine (X3), dried, filtered and evaporated in vacuo to give the title compound as a yellow oil (0.92 g, 2.6 mmol). $^1$H-NMR δ (CDCl$_3$) 7.42–7.20 (10H, m), 4.98 (2H, s), 4.45 (1H, m), 3.62 (1H, dd, J=4.4, 14.1 Hz), 3.12 (1H, dd, J=5.9, 17.1 Hz), 3.00 (1H, dd, J=10, 14.1 Hz) and 2.73 (1H, dd, J=6.2, 17.1 Hz).

STEP I 3-(4-Methyl-piperidine-1-sulfonyl)-4-phenyl-butyric Acid Benzyl Ester

The product from Step H (0.92 g, 2.6 mmol) was taken up in DCM (25 mL) with stirring and cooled to 0° C. TEA (362 μL, 2.6 mmol) and 4-methyl-piperidine (307 μL, 2.6 mmol) were added and the reaction warmed to room temperature and stiired overnight. The reaction was diluted with DCM and washed successively with water, 1 M HCl, water, brine, dried, filtered and concentrated in vacuo to give a yellow oil. This was purified by silica gel column chromatography eluting with hex /EtOAc 8:2 to give the titled compound as a yellow oil (440 mg, 41%). $^1$H-NMR δ (CDCl$_3$) 7.40–7.18 (10H, m), 5.0 (1H, d, J=12.2 Hz), 4.95 (1H, d, J=12.2 Hz), 3.9 (1H, m), 3.68 (2H, m), 3.42–3.31 (1H, dd, J=4.4, 14.1 Hz), 2.91–2.80 (1H, dd, J=5.9, 17.1 Hz), 2.79–2.62 (3H, m), 2.58–2.47 (1H, dd, J=6.2, 17.1 Hz), 1.69–135 (2H, m), 1.30–1.10 (3H, m) and (3H, d, J=6.2 Hz).

STEP J 3-(4-Methyl-piperidine-1-sulfonyl)-4-phenyl-butyric Acid

The product from Step 1 (440 mg, 1.06 mmol) was converted to the title compound using the method in Step F using MeOH (10 mL) as the reaction solvent. Oil (270 mg, 78%). $^1$H-NMR δ(MeOD) 7.29 (5H, m), 3.88 (1H, m), 3.67 (2H, m), 3.23 (1H, dd, J=4.3, 12.8 Hz), 2.84 (4H, m), 2.45 (1H, dd, J=4.3, 12.8 Hz), 1.63 (2H, m), 1.47 (1H, m), 1.17 (2H, m) and 0.93 (3H, d, J=6.4 Hz). $^{13}$C-NMR δ(MeOD) 174.2, 138.8, 130.8, 130.2, 128.4, 61.0, 47.6, 36.6, 35.7, 34.7, 32.0, 22.5. ESMS=(M+Na) 348.2, (M−1) 323.8.

EXAMPLE 4

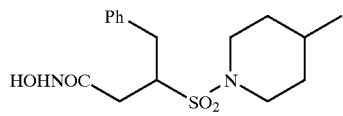

N-Hydroxy-3-(4-Methylpiperidine-1-sulfonyl)-4-phenyl-butyramide.

The product from Step J (270 mg, 0.83 mmol) was converted to the title compound using the method in Step G to give the title compound as a pink gum (129 mg). ¹H-NMR δ(MeOD) 7.31 (5H, m), 3.97 (1H, m), 3.63 (2H, m), 3.24 (1H, dd, J=4.9, 14.2 Hz), 2.79 (3H, m), 2.51 (1H, dd, J=7.5, 15.6 Hz), 2.26 (1H, dd, J=4.9, 14.2 Hz), 1.60 (2H, m), 1.46 (1H, m), 1.14 (2H, m) and 0.92 (3H, d, J=6.39 Hz). ¹³C-NMR δ(MeOD) 169.5, 138.9, 130.7, 130.1, 128.4, 59.9, 47.4, 36.7, 35.7, 33.3, 32.0, 22.5. ESMS=(M+Na) 363.0, (M31 1) 338.8.

EXAMPLE 5

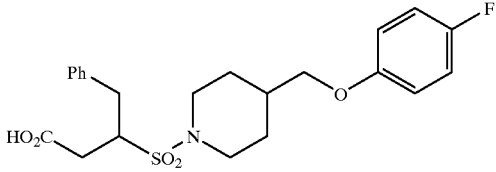

3-[4-(4-Fluoro-phenoxymethyl )-piperidime-1-sulfonyl]-4-phenyl-butyric Acid

Pink gum. ¹H-NMR δ(MeOD) 7.35–7.20 (5H, m), 7.12–6.84 (4H, m), 3.91 (1H, m), 3.79–3.76 (4H, m), 3.31 (1H, m), 2.90–2.66 (4H, m), 2.49–2.41 (1H, dd, J=4.4 17.2 Hz), 2.0–1.70 (3H, m) and 1.43–1.22 (2H, m). ¹³C-NMR δ(MeOD) 174.3, 160.9, 157.1, 138.8, 130.8, 130.2, 128.5, 117.2, 117.1, 116.9, 116.8, 74.2, 61.1, 47.2, 37.3, 36.6, 34.8, 30.5. IR $V_{max}$ (reflection disc) 2947, 1730, 1598, 1503, 1409, 1253, 1054, 1030, 948, 829, 699. ESMS=(M+1) 436.0, (M+TFA-1) 548.0, (M-1) 433.8.

EXAMPLE 6

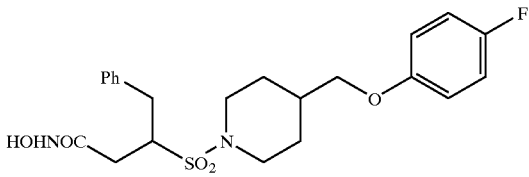

3-[4-(4-Fluoro-phenoxymethyl)-piperidine-1-sulfonyl]-N-hydroxy-4-phenyl-butyramide Pale pink foam. ¹H-NMR δ(MeOD) 7.40–7.26 (5H, m), 7.01–6.84 (4H, m), 4.13 (1H, m), 3.78–3.72 (4H, m), 3.24 (1H, m), 2.81–2.74 (3H, m), 2.59–2.50 (1H, dd, J=7.6 15.7 Hz), 2.30–2.22 (1H, dd, J=4.4, 15.7 Hz), 2.02–1.80 (3H, m) and 1.47–1.20 (2H, m). ¹³C-NMR δ(MeOD) 169.5, 160.9, 157.1, 138.9, 130.7, 130.2, 128.4, 117.2, 117.1, 117.0, 116.8, 74.2, 60.0, 47.0, 37.3, 36.6, 33.3, 30.5. IR $V_{max}$ (reflection disc) 3293, 2919, 1664, 1503, 1449, 1307, 1208, 1136, 1044, 937, 828, 751. ESMS=(M+Na) 473.2, (M+TFA-1) 563.2.

EXAMPLE 7

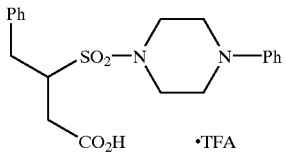

4-Phenyl-3-(4-phenyl-piperazine-1-sulfonyl)-butyric Acid; Compound with Trifluoro-acetic Acid.

Pale pink foam. ¹H-NMR δ(MeOD) 7.50–7.20 (7H, m), 7.20–6.99 (3H, m), 4.01 (1H, m), 3.50 (4H, m), 3.40–3.20 (5H, m), 2.89–2.80 (1H, dd, J=7.3, 17.2 Hz), 2.80–271 (1H, dd, J=7.3, 17.2 Hz) and 2.54–2.46 (1H, dd, J=4.3, 17.2 Hz). ¹³C-NMR δ(MeOD) 174.2, 150.2, 138.7, 131.0, 130.8, 130.3, 128.6, 124.7, 119.6, 61.2, 52.8, 46.7, 36.4, 34.8. IR $V_{max}$ (reflection disc) 3030, 1726, 1661, 1494, 1442, 1324, 1267, 1143, 942. ESMS=(M+1) 388.8, (M-1) 387.0.

EXAMPLE 8

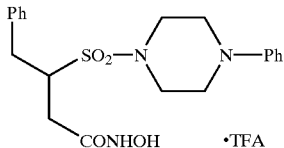

N-Hydroxy-4-phenyl-3-(4-phenyl-piperazine-1-sulfonyl)-butyramide; Compound with Trifluoro-acetic Acid.

Pink foam. ¹H-NMR δ(MeOD) 7.33–7.23 (7H, m), 7.10–6.96 (3H, m), 4.09 (1H, m), 3.42–3.36 (5H, m), 3.29 (4H, m), 2.88–2.78 (1H, dd, J=8, 16 Hz), 2.62–2.52 (1H, dd, J=8, 16 Hz) and 2.33–2.25 (1H, dd, J=4.3, 16 Hz). ¹³C-NMR δ(MeOD) 169.6, 150.2, 138.7, 131.0, 130.8, 130.3, 128.6, 124.9, 119.7, 60.1, 52.8, 46.8, 36.3, 33.3. IR $V_{max}$ (reflection disc) 3189, 1668, 1493, 1446, 1143, 945. ESMS=(M+1) 404.0, (M-1) 402.0.

EXAMPLE 9

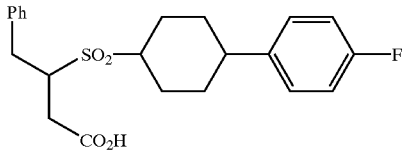

3-[4-(4-Fluoro-phenyl)-piperidine-1-sulfonyl]-4-phenyl-butyric Acid

White solid. ¹H-NMR δ(MeOD) 7.45–7.19 (7H, m), 7.03–6.97 (2H, m), 3.99 (1H, m), 3.87–3.81 (2H, bm), 3.37 (1H, m), 3.0–2.60 (5H, m), 2.50 (1H, dd, J=4.1, 17.2 Hz), 1.90–1.79 (2H, m) and 1.73–1.56 (2H, m). ¹³C-NMR δ(MeOD) 174.3, 165.2, 161.4, 143.1, 138.8, 130.8, 130.2, 130.0, 129.8, 128.5, 116.6, 116.3, 61.0, 47.9, 42.9, 36.6, 35.0, 34.9. ESMS=(M+Na) 428.2, (M—1) 404.0.

EXAMPLE 10

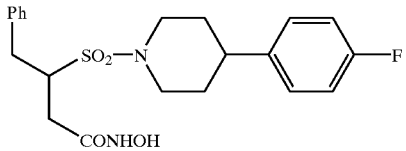

3-[4-(4-Fluoro-phenyl)-piperidine-1-sulfonyl]-N-hydroxy-4-phenyl-butyramide

White solid. ¹H-NMR δ(MeOD) 7.40–7.20 (7H, m), 7.22–6.96 (2H, m), 4.05 (1H, m), 3.81–3.77 (2H, bm), 3.30 (1H, m), 3.02–2.85 (3H, bm), 2.77–2.55 (2H, bm), 2.30–2.34 (1H, bdd), 1.90–1.80 (2H, m) and 1.75–1.55 (2H, m). ¹³C-NMR δ(MeOD) 169.5, 165.2, 161.4, 143.2, 139.0, 130.8, 130.2, 130.0, 129.8, 128.4, 116.6, 116.2, 59.9, 47.7, 47.6, 43.0, 36.6, 35.0, 34.9, 33.4. IR $V_{max}$ (ATR) 2922, 1653, 1508, 1448, 1306, 1218, 1134, 1050, 939, 823, 739, 699. ESMS=(M+Na)443.0, (M+TFA-1) 533.2, (M-1) 418.8.

In examples 11–18 a tert-butyl ester was used in place of the benzyl ester (Step C). The method for its preparation is described (Step K) and Step L replaces Step F.

EXAMPLE 11

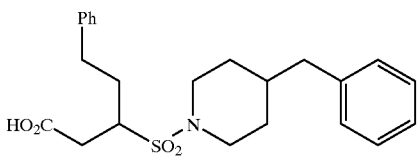

3-(4-Benzy-piperidine-1-sulfonyl)-5-phenyl-pentanoic Acid

STEP K
3-Acetylsulfanyl-5-phenyl-pentanoic acid tert-butyl ester

3-Acetylsulfanyl-5-phenyl-pentanoic acid was taken up in DCM (15 mL) with stirring in a pressure bottle. c.$H_2SO_4$ (1 mL) was added and the solution cooled to −78° C. Isobutylene gas was bubbled through this solution until the volume had doubled. The pressure vessel was sealed and allowed to warm to room temperature and stirred overnight. The reaction was re-cooled to −78° C. and opened and warmed to room temparature. The excess isobuylene gas was allowed to evaporate and then the reaction solution was poured into a stirred 1 M $Na_2CO_3$ solution. The product was extracted into DCM and washed with brine, dried and filtered and evaporated under reduced pressure to give an orange oil (10.64 g, 34.5 mmol). $^1$H-NMR δ($CDCl_3$) 7.27–7.14 (5H, m), 3.88 (1H, m), 2.80–2.51 (4H, m), 2.34 (3H, s), 1.97–1.84 (2H, m) and 1.43 (9H, s).

STEP L
3-(4-Benzy-piperidine-1-sulfonyl)-5-phenyl-pentanoic Acid 3-(4-Benzy-piperidine-1-sulfonyl)-5-phenyl-pentanoic acid tert-butyl ester (1.04 g, 2.2 mmol) was taken up in DCM (5 mL) with stirring and cooled to 0° C. TFA (5 mL) was added slowly and the resulting solution placed in the fridge overnight. Solvents evaporated under reduced pressure to give the title compound as a yellow oil (913 mg, Quant). $^1$H-NMR δ(MeOD) 7.56–7.11 (10H, m), 3.66–3.56 (3H, m), 2.90–2.59 (6H, m), 2.51 (2H, d, J=6.7 Hz), 2.20 (1H, m), 1.90 (1H, m), 1.62–1.47 (3, m) and 1.25–1.11 (2H, m). $^{13}$C-NMR δ(MeOD) 174.5, 142.6, 141.7, 130.6, 130.1, 130.0, 129.7, 127.7, 127.4, 58.7, 47.6, 44.2, 39.2, 35.5, 33.9, 33.7, 33.0. IR $V_{max}$ (ATR) 2915, 1709, 1451, 1304, 1133, 1041, 937, 746, 698. ESMS=(M+1) 416.0, (M−1) 414.0.

EXAMPLE 12

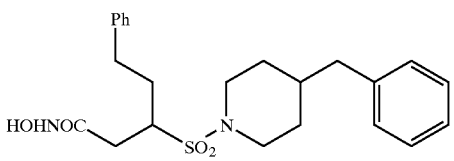

3-(4-Benzy-piperidine-1l-sulfonyl )-5-phenyl-pentanoic Acid Hydroxyamide

Off-white foam. $^1$H-NMR δ(MeOD) 7.40–7.13 (10H, m), 3.66–3.50 (3H, m), 2.88–2.58 (5H, m), 2.52 (2H, d, J=6.7 Hz), 2.39 (1H, dd, J=6.7, 15.3 Hz), 2.10 (1H, m), 1.89 (1H, m), 1.79–1.47 (3H, m) and 1.22–1.08 (2H, m). $^{13}$C-NMR δ(MeOD) 169.6, 142.8, 141.7, 130.6, 130.1, 130.0, 129.7, 127.7, 127.4, 58.1, 47.6, 44.2, 39.2, 34.2, 33.9, 33.7, 33.1. IR $V_{max}$ (ATR)2917, 1655, 1451, 1303, 1134, 1042, 937, 746, 698. ESMS=(M+1) 431.2, (M−1) 429.0, (M+TFA−1) 543.0.

EXAMPLE 13

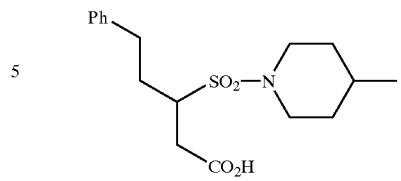

3-(4-Methyl-piperidine-1-sulfonyl)-5-phenyl-pentanoic acid

Tan solid. $^1$H-NMR δ(MeOD) 7.51–7.15 (5H, m), 3.80–3.51 (3H, m), 2.95–2.60 (6H, m), 2.17 (1H, m), 1.90 (1H, m), 1.81–1.61 (2H, m), 1.45 (1H, m), 1.30–0.99 (2H, m), 0.92 (3H, d, J=6.5 Hz). $^{13}$C-NMR δ(MeOD) 174.5, 142.6, 130.0, 127.7, 58.7, 47.7, 35.7, 35.5, 33.9, 33.0, 32.1, 22.5. IR $V_{max}$ (ATR) 2924, 2866, 1710, 1453, 1301, 1161, 1132, 1049, 927, 747, 699. ESMS=(M+Na) 362.2, (M−1) 338.2.

EXAMPLE 14

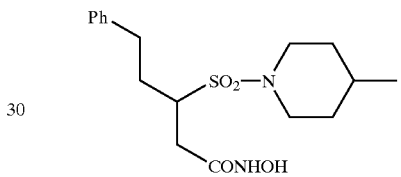

3-(4-Methyl-piperidine-1-sulfonyl)-5-phenyl-pentanoic Acid Hydroxyamide

Yellow oil. $^1$H-NMR δ(MeOD) 7.31–7.17 (5H, m), 3.70–3.61 (3H, m), 2.88–2.61 (5H, m), 2.40 (1H, dd, J=6.9, 15.3 Hz), 2.13 (1H, m), 1.89 (1H, m), 1.66–1.56 (2H, m), 1.48 (1H, m), 1.22–1.03 (2H, m) and 0.93 (3H, d, J=6.5 Hz). $^{13}$C-NMR δ(MeOD) 169.5, 142.8, 130.0, 127.7, 58.1, 47.6, 35.7, 34.2, 33.9, 33.1, 32.1, 22.5. IR $V_{max}$ (ATR)2922, 1655, 1438, 1302, 1161, 1134, 1049, 928, 747, 695. ESMS=(M+Na) 377.2, (M−1) 353.2.

EXAMPLE 15

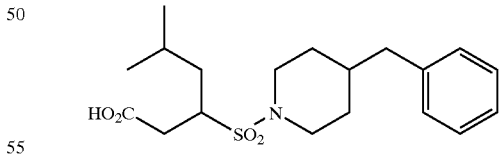

3-(4-Benzyl-piperidine-1-sulfonyl)-5-methyl-hexanoic Acid

Yellow oil. $^1$H-NMR δ(MeOD) 7.45–7.13 (5H, m), 3.84–3.60 (2H, m), 3.59 (1H, m), 2.91–2.72 (2H, m), 2.68–2.46 (4H, m), 1.82–1.63 (5H, m), 1.50 (1H, m), 1.39–1.03 (2H, m), 0.96 (3H, d, J=6.2 Hz) and 0.91 (3H, d, J=6.2 Hz). $^{13}$C-NMR δ(MeOD) 174.6, 141.7, 130.5, 129.7, 127.5, 58.2, 47.9, 47.7, 44.2, 39.8, 39.3, 35.9, 33.7, 27.0, 23.9, 22.3. IR $V_{max}$ (ATR) 2924, 1709, 1449, 1320, 1128, 1042, 937, 747, 699. ESMS=(M+Na) 390.0, (M−1) 366.0.

EXAMPLE 16

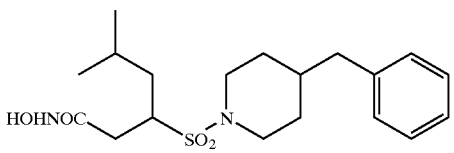

3-(4-Benzyl-piperidine-1-sulfonyl)-5-methyl-hexanoic Acid Hydroxyamide

Off-white foam. $^1$H-NMR δ(MeOD) 7.28–7.13 (15H, m), 3.72–3.59 (3H, m), 2.84–2.75 (2H, m), 2.69–2.59 (3H, m), 2.24 (1H, dd, J=6.1, 15.6 Hz), 1.79–1.64 (5H, m), 1.45, (1H, m), 1.36–1.12 (2H, m) 0.94 (3H, d, J=6.3 Hz) and 0.91 (3H, d, J=6.3 Hz) $^{13}$NMR δ(MeOD) 169.5, 141.7, 130.6, 129.7, 127.4, 57.4, 47.8, 47.6, 44.2, 40.0, 39.7, 34.7, 33.8, 27.0, 23.8, 22.5. IR $V_{max}$ (ATR) 2927, 1657, 1451, 1320, 1130, 1042, 940, 746, 699. ESMS=(M+Na) 405.0, (M−1) 381.0.

EXAMPLE 17

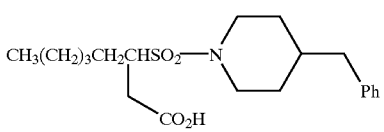

3-(4-Benzyl-piperidine-1-sulfonyl)-octanoic Acid

Yellow oil. $^1$H-NMR δ(MeOD) 7.44–7.13 (5H, m), 3.73–3.68 (2H, m), 3.52 (1H, m), 2.90–2.77 (3H, m), 2.75–2.48 (3H, m), 2.0–1.80 (1H, m), 1.80–1.17 (12H, m) and 0.91 (3H, t, J=6.7 Hz). $^{13}$C-NMR δ(MeOD) 174.6, 141.7, 130.6, 129.7, 127.4, 59.7, 47.9, 47.6, 44.2, 39.3, 35.5, 33.7, 33.1, 30.8, 27.6, 23.8,14.7. IR $V_{max}$(ATR) 2923, 2853, 1709, 1451, 1304, 1135, 1042, 937, 746, 699. ESMS=(M+1) 382.0, (M−1) 379.8.

EXAMPLE 18

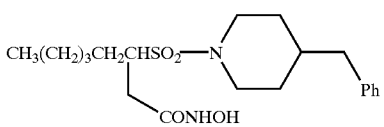

3-(4-Benzyl-piperidine-1-sulfonyl)-octanoic Acid Hydroxyamide

Yellow oil. $^1$H-NMR δ(MeOD) 7.28–7.13 (5H, m), 3.72–3.67 (2H, m), 3.62–3.52 (1H, m), 2.96–2.76 (2H, m), 2.60–2.51 (3H, m), 2.32 (1H, dd, J=6.7, 15.4 Hz), 1.92–1.69 (1H, m), 1.69–1.18 (12H, m) and 0.91 (3H, t, J=6.7 Hz). $^{13}$C-NMR δ(MeOD) 169.7, 141.7, 130.6, 129.7, 127.4, 58.9, 47.8, 47.5, 44.2, 39.3, 34.1, 33.8, 33.2, 30.8, 27.6, 23.8, 14.7. IR $V_{max}$(ATR) 2923, 2854, 1656, 1452, 1304, 1137, 1042, 938, 746, 699. ESMS=(M+1) 397.2, (M−1) 395.0, (M+TFA−1) 509.0.

In Vitro MMP Assay and Inhibitor IC$_{50}$ Determination

The potency of compounds of the invention as inhibitors of collagenase may be determined by the procedure of Cawston and Barrett, (Anal. Biochem., 99, 340–345, 1979), whereby a 1mM solution of the compound being tested, or a dilution thereof, is incubated at 37° for 16 hours with collagen and collagenase (buffered with 25mM Hepes, pH 7.5 containing 5mM CaCl$_2$, 0.05% Brij 35 and 0.02% NaN$_3$). The collagen is acetylated $^{14}$C collagen prepared by the method of Cawston and Murphy, (Methods in Enzymology, 80, 711, 1981). The samples are centrifuged to sediment undigested collagen, and an aliquot of the radioactive supernatant removed for assay on a scintillation counter as a measure of hydrolysis. The collagenase activity in the presence of 1mM of the test compound, or a dilution thereof, is compared to activity in a control devoid of inhibitor and the result reported as that of inhibitor concentration effecting 50% inhibition of the collagenase activity (IC$_{50}$). The potency of compounds of the invention as inhibitors of stromelysin may be determined by the procedure of Cawston et al, (Biochem. J., 195, 159–165, 1981), whereby a 1mM solution of the compound being tested, or a dilution thereof, is incubated at 37° for 16 hours with stromelysin and $^{14}$C acetylate casein (buffered with 25mM Hepes, pH 7.5 containing 5mM CaCl$_2$, 0.05% Brij 35 and 0.02% NaN$_3$). The casein is acetylated $^{14}$C casein prepared by the method of Cawston et al (ibid). The stromelysin activity in the presence of 1mM of the test compound, or a dilution thereof, is compared to activity in a control devoid of inhibitor and the result reported as that of inhibitor concentration effecting 50% inhibition of the stromelysin activity (IC$_{50}$).

The potency of compounds of the invention as inhibitors of 72 kDa gelatinase may be determined by a procedure based on the method of Sellers et. al, Biochem. J., 171, 493–496 (1979). 72 kDa gelatinase, derived from RPMI-7951 cells is purified by gelatin-agarose chromatography. The enzyme is activated by incubation with aminophenyl mercuric acetate and approximately 0.05 units is incubated with 50μg [$^{14}$C]-radiolabellet gelatin in an appropriate buffer for 16 hours at 37° C. At the end of the incubation 50μg bovine serum albumin, together with trichloroacetic acid (final concentration 16%) are added to stop the reaction and to precipitate any undegraded substrate. The reaction tubes are placed on ice for 15 minutes before centrifugation at 10,000g for 15 minutes to sediment the precipitated substrate. A 200μl aliquot of the reaction supernatant is removed and the radioactivity determined by liquid scintillation counting. The effect of the inhibitors is determined by reference to a dose response curve. The IC$_{50}$ (the concentration of inhibitor required to cause a 50% decrease in enzyme activity) is obtained by fitting a curve to the data and computing the concentration of inhibitor required to achieve 50% inhibition of the enzyme. For each IC$_{50}$ determination, the effect on gelatinase activity of at least 8 concentrations of the inhibitor are examined. The inhibitors are dissolved and diluted in DMSO.

What is claimed is:

1. A pharmaceutical composition comprising a compound of formula (I) or a pharmaceutically acceptable salt, hydrate or solvate thereof, together with a pharmaceutically acceptable carrier

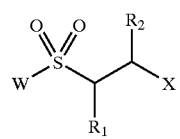

(I)

wherein
X represents a carboxylic acid group —COOH;
R$_2$ represents a radical of formula (II)

$$R_3—(ALK)_m—(Q)_p—(ALK)_n—$$ (II)

wherein
- R$_3$ represents hydrogen or an optionally substituted cycloalkyl, optionally substituted cycloalkenyl, optionally substituted aryl, or optionally substituted heterocyclic ring having 5 or 6 ring members,
- each ALK independently represents an optionally substituted divalent C$_1$–C$_3$ alkylene radical,
- Q represents —O—, —S—, —S(O)—, —S(O$_2$)—, —C(O)O—, —OC(O)— or —N(R$_9$)—wherein R$_9$ is hydrogen, C$_1$–C$_6$alkyl, or C$_1$–C$_6$alkoxy, and
- m, n and p are independently 0 or 1;

R$_1$ represents a radical of formula (II) as defined for R$_2$, except that R$_1$ is not hydrogen;

W represents a cyclic amino radical of formula (IIIA)

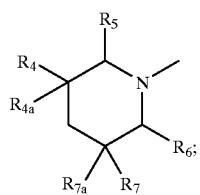

(IIIA)

and
- (i) R$_4$, R$_5$, R$_6$ and R$_7$ each independently represents a radical of formula (II) as defined in relation to R$_2$, and R$_{4a}$ and R$_{7a}$ each independently represent hydrogen or C$_1$–C$_3$ alkyl, or
- (ii) R$_4$, R$_{4a}$ and R$_5$ taken together with the carbon atoms to which they are attached form an optionally substituted benzene or pyridine ring fused to the cyclic amine ring, R$_{7a}$ represents hydrogen or C$_1$–C$_3$ alkyl, and R$_6$ and R$_7$ each independently represents a radical of formula (II) as defined in relation to R$_2$, or
- (iii) R$_4$, R$_{4a}$ and R$_5$ taken together with the carbon atoms to which they are attached form an optionally substituted benzene or pyridine ring fused to the cyclic amine ring, R$_6$, R$_7$ and R$_{7a}$ taken together with the carbon atoms to which they are attached also form an optionally substituted benzene or pyridine ring fused to the cyclic amine ring, or
- (iv) when W is a cyclic amino radical of formula (IIIA) wherein Y is —(CH(R$_8$))—, then R$_4$, R$_{4a}$ and R$_8$ taken together with the carbon atoms to which they are attached form an optionally substituted benzene or pyridine ring fused to the cyclic amine ring, R$_{7a}$ represents hydrogen or C$_1$–C$_3$ alkyl, and R$_5$, R$_6$ and R$_7$ each independently represents a radical of formula (II) as defined in relation to R$_1$ and R$_2$, or
- (v) when W is a cyclic amino radical of formula (IIIB) then R$_4$, R$_{4a}$, R$_7$ and R$_{7a}$ taken together with the carbon atoms to which they are attached form an optionally substituted benzene or pyridine ring fused to the cyclic amine ring, and R$_5$ and R$_6$ each independently represents a radical of formula (II) as defined in relation to R$_1$ and R$_2$, and wherein optional substituents in any of the above groups are selected from the group consisting of (C$_1$–C$_3$)alkyl, (C$_1$–C$_3$)alkoxy, oxo, phenyl, phenoxy, hydroxy, mercapto, (C$_1$–C$_6$)alkylthio, amino, halo, trifluoromethyl, cyano, nitro, —COOH, —CONH$_2$, —COOR$^A$, —NHR$^A$, —NR$^A$R$^B$, and CONR$^A$R$^B$, wherein R$^A$ and R$^B$ are independently (C$_1$–C$_3$)alkyl.

2. A composition as claimed in claim 1 wherein R$_1$ is an optionally substituted C$_1$–C$_6$alkyl, phenyl, or phenyl (C$_1$–C$_6$alkyl)— group.

3. A composition as claimed in claim 2 wherein R$_1$ is n-propyl, iso-propyl n-butyl, iso-butyl, benzyl, phenylethyl, 4-fluorobenzyl, or 4-fluorophenylethyl.

4. A composition as claimed in claim 1 wherein R$_2$ is hydrogen, or an optionally substituted C$_1$–C$_6$alkyl, phenyl (C$_1$–C$_6$alkyl)— group, or an optionally substituted heterocyclic group.

5. A composition as claimed in claim 4 wherein R$_2$ is hydrogen, n-propyl, n-butyl, iso-butyl, benzyl, phenylethyl, tetrahydropyranyl, 1-(3,4,4-trimethyl-2,5-dioxoimidazolidin-1-yl)propyl, or 1-(phthalimido)-propyl.

6. A composition as claimed in claim 1 wherein W is a radical of formula (IIIC),

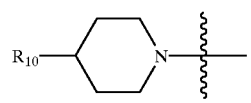

(IIIC)

wherein R$_{10}$ is as defined for R$_2$ in claim 1.

7. A composition as claimed in claim 6 wherein R$_{10}$ is an optionally substituted phenyl, biphenyl, phenyl (C$_1$–C$_6$alkyl)-, phenoxy, phenoxy(C$_1$–C$_3$)alkyl, or heterocyclic group.

8. A composition as claimed in claim 6 wherein R$_{10}$ is n-propyl, n-butyl or iso-butyl; or a phenyl, phenoxy, benzyl, phenylethyl, phenylpropyl, phenoxy, or phenoxymethyl group, any of which may be substituted in the phenyl ring; pyridinyl or pyridinyloxy either of which may be substituted by chloro, fluoro, methoxy or cyano; or biphenyl or 4-pyridinylphenyl, either of which may be substituted in either ring by chloro, fluoro, methoxy or cyano.

9. A composition as claimed in claim 6 wherein W is 4-phenylmethylpipeddinyl, 4-methylpiperidinyl, 4-(4-methylphenyl)piperidinyl, 4-(4-chlorophenoxy)piperidinyl, 4-phenylpiperidinyl, 4-(4-fluorophenyl)piperidinyl, 4-(4-fluorophenoxy)piperidinyl, 4-(4-pyridinyloxy)-piperidinyl, 4-(4-cyanophenyloxy)piperidinyl, 4-(4-cyanophenoxyimino)-piperdinyl, 4-(4'-chloro-biphenyl-4-yl)-piperdinyl, 4-(2-chloro-biphenyl-4-yl) piperdinyl, 4-(4-fluorophenylmethyl)piperidinyl, or 4-(4-fluorophenoxymethyl)-piperidinyl.

* * * * *